United States Patent
Berndl et al.

(10) Patent No.: US 9,060,936 B2
(45) Date of Patent: *Jun. 23, 2015

(54) DOSAGE FORMS WITH IMPROVED BIOAVAILABILITY

(75) Inventors: Gunther Berndl, Herheim Am Berg (DE); Matthias Degenhardt, Ludigshafen (DE); Markus Maegerlein, Mannheim (DE)

(73) Assignee: Abbvie Deutschland GmbH & Co. KG, Wiesbaden (DE)

( * ) Notice: Subject to any disclaimer, the term of this patent is extended or adjusted under 35 U.S.C. 154(b) by 61 days.

This patent is subject to a terminal disclaimer.

(21) Appl. No.: 13/165,398

(22) Filed: Jun. 21, 2011

(65) Prior Publication Data

US 2011/0311595 A1 Dec. 22, 2011

Related U.S. Application Data

(63) Continuation of application No. 11/997,325, filed as application No. PCT/EP2006/007840 on Aug. 8, 2006, now abandoned.

(60) Provisional application No. 60/595,818, filed on Aug. 8, 2005.

(51) Int. Cl.
  *A61K 9/14* (2006.01)
  *A61K 9/16* (2006.01)

(52) U.S. Cl.
  CPC ............... *A61K 9/145* (2013.01); *A61K 9/146* (2013.01); *A61K 9/1617* (2013.01); *A61K 9/1652* (2013.01)

(58) Field of Classification Search
  CPC ..... A61K 9/145; A61K 9/146; A61K 9/1617; A61K 9/1652
  See application file for complete search history.

(56) References Cited

U.S. PATENT DOCUMENTS

| | | | |
|---|---|---|---|
| 4,267,179 A | 5/1981 | Heeres et al. | |
| 6,509,038 B2 | 1/2003 | Baert et al. | |
| 8,486,456 B2 * | 7/2013 | Berndl et al. | 424/489 |
| 2004/0014817 A1 | 1/2004 | Rosenberg et al. | |
| 2004/0197398 A1 | 10/2004 | Friesen et al. | |
| 2005/0084529 A1 | 4/2005 | Rosenberg et al. | |
| 2009/0214656 A1 | 8/2009 | Berndl et al. | |
| 2014/0005204 A1 * | 1/2014 | Berndl et al. | 514/254.07 |

FOREIGN PATENT DOCUMENTS

| | | |
|---|---|---|
| EP | 0 240 904 A2 | 10/1987 |
| EP | 0 240 906 A2 | 10/1987 |
| EP | 0 337 256 A2 | 10/1989 |
| EP | 1 323 416 A1 | 7/2003 |
| WO | WO-93/19061 A1 | 9/1993 |
| WO | WO-97/44014 A | 11/1997 |
| WO | WO-02/24184 A2 | 3/2002 |
| WO | WO-2004/054568 A | 7/2004 |
| WO | WO-2007017248 A2 | 2/2007 |

OTHER PUBLICATIONS

U.S. Appl. No. 11/997,256, filed Feb. 15, 2007, Berndl et al.
Form PCT/ISA/210-ISR for PCT/EP2006/007839, Mar. 29, 2007, Abbott GMBH & CO KG.
Form PCT/ISA/237—Written Opinion for PCT/EP2006/007839, Mar. 29, 2007, Abbott GMBH & CO KG.
Form PCT/IB/373 issued in PCT/EP2006/007839 (IPRP), Feb. 12, 2008, Abbott GMBH & CO KG.
Form PCT/ISA/210-ISR for PCT/EP2006/007840, Feb. 15, 2007, Abbott GMBH & CO KG.
Form PCT/ISA/237—Written Opinion for PCT/EP2006/007840, Feb. 8, 2008, Abbott GMBH & CO KG.
Verreck Geert et al., "Characterization of solid dispersions of itraconazole and hydroxypropylmethylcellulose prepared by melt extrusion: Part I," International Journal of Pharmaceutice (Kidlington), vol. 251, No. 1-2, Jan. 30, 2003, pp. 165-174.
Leuner, C. et al., "Improving drug solubility for oral delivery using solid dispersions," European Journal of Pharmaceutics and Biopharmaceutics, Elsevier Science Publishers B.V., Amsterdam, NL, vol. 50, No. 1, 3 Jul. 2000, pp. 47-60.
Negroni R et al; "Itraconazole: Pharmacokinetics and Indications", Archives of Medical Research, Instituto Mexicano Del Seguro Social, Mexico, MX, 1993, pp. 387-393, XP000569636, ISSN: 0188-4409.

* cited by examiner

*Primary Examiner* — Aradhana Sasan
(74) *Attorney, Agent, or Firm* — Saul Ewing LLP; Peter C. Lauro, Esq.

(57) ABSTRACT

A solid dispersion product comprising an effective amount of one or more active ingredients and an effective amount of one or more hydroxypropyl methylcellulose(s), which satisfies the Formula $0.35 > \Delta H_{tr}$ (1) (wherein $\Delta H_{tr}$ represents the endotherm (J/g) accompanying a transition at about 240° C.). The solid dispersion product is used for the manufacture of a dosage form having improved bioavailability of said one or more active ingredients by oral administration to a patient in need thereof.

31 Claims, No Drawings

DOSAGE FORMS WITH IMPROVED BIOAVAILABILITY

This application is a continuation of U.S. application Ser. No. 11/997,325, which is the U.S. national phase, pursuant to 35 U.S.C. §371, of PCT international application Ser. No. PCT/EP2006/007840, filed Aug. 8, 2006, designating the United States and published in English on Feb. 15, 2007 as publication no. WO 2007/017249 A1, which claims priority to U.S. provisional application Ser. No. 60/595,818, filed Aug. 8, 2005. The entire contents of the aforementioned patent applications are incorporated herein by this reference.

The present invention relates to novel dosage forms with improved bioavailability as well as to processes for their preparation.

A measure of the potential usefulness of an oral dosage form of a pharmaceutical agent is the bioavailability observed following oral administration of said dosage form. Various factors can affect the bioavailability of a drug when administered orally. These factors include aqueous solubility, drug absorption throughout the gastrointestinal tract, dosage strength and first pass effect. Aqueous solubility is one of the most important of these factors. Unfortunately, many active ingredients are typically characterized by poor aqueous solubility.

For a variety of reasons, such as patient compliance and taste-masking, a solid dosage form is usually preferred over a liquid dosage form. In most instances, however, solid oral dosage forms of a drug provide a lower bioavailability than oral solutions of the drug.

There have been attempts to improve the bioavailability provided by solid dosage forms by forming solid dispersions or solid solutions of the drug. Solid solutions are preferred physical systems because the components therein readily form liquid solutions when brought into contact with a liquid medium such as gastric juice. This increased propensity for dissolution may be attributed at least in part to the fact that the energy required for dissolving the components from a solid solution is less than that required for dissolving the components from a crystalline or microcrystalline solid phase.

A continuous process for producing solid pharmaceutical forms, including solid solution products, has been known for some time; it entails converting a melt of polymeric binder that contains active ingredients and that is free from solvents into the required drug form by injection molding or extrusion and subsequent shaping (see, for example, EP-A-240 904, EP-A-240 906 and EP-A-337 256). Hydroxypropyl methylcellulose is an example of a particularly preferred polymeric binder.

EP-A-1 323 416 exemplifies the preparation of solid dispersions from an active ingredient and hydroxypropyl methylcellulose. The reference reports that fibrous materials occurred when the solid dispersion was pulverized. Presumably, the occurrence of fibrous material is indicative of a less than optimal homogeneity of the solid dispersion product.

It is desirable to provide hydroxypropyl methylcellulose-based dosage forms with still greater bioavailability.

This objective is met by a solid dispersion product comprising (i) an effective amount of one active ingredient or a mixture of two or more active ingredients and (ii) an effective amount of a hydroxypropyl methylcellulose or a mixture of two or more hydroxypropyl methylcelluloses which solid dispersion product satisfies the formula $$0.35 > \Delta H_{tr}$$

(wherein $\Delta H_{tr}$ represents the endotherm (J/g) accompanying a transition at an endothermic peak temperature in the range of from about 230° C. to about 260° C.).

Preferably, the solid dispersion product satisfies the formula $$0.20 > \Delta H_{tr}$$

More preferably, the solid dispersion product satisfies the formula $$0.15 > \Delta H_{tr}$$

The $\Delta H_{tr}$ is determined by differential scanning calorimetry (DSC) measurement. More specifically, a melting endotherm curve is first prepared by the following method using a differential scanning calorimeter. A finely ground sample of the dispersion product is placed in an open aluminium pan of a differential scanning calorimeter. The endotherm between −20° C. and 300° C. is obtained by heating the sample at a temperature rise rate of 10° C./minute. A maximum peak is observed in the thus prepared melting endotherm curve in the range of from about 230° C. to about 260° C., preferably 240° C. to about 250° C., (in the following also referred to as "endotherm at about 240° C."), and the change rate of enthalpy observed thereupon, in terms of Joules per one gram of solid dispersion product, is determined to be the endotherm $\Delta H_{tr}$. The change rate of enthalpy corresponds to the area enclosed between the peak and the interpolated base line.

The term "solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogeneous throughout or consists of one phase (as defined in thermodynamics), such a dispersion is called a "solid solution". Solid solutions are preferred physical systems because the components therein readily form liquid solutions when brought into contact with a liquid medium such as gastric juice. This increased propensity for dissolution may be attributed at least in part to the fact that the energy required for dissolving the components from a solid solution is less than that required for dissolving the components from a crystalline or microcrystalline solid phase.

The term "solid dispersion product" also comprises dispersions which are less homogeneous throughout than solid solutions. Such dispersions are not chemically and physically uniform throughout or comprise more than one phase. These encompass systems having small particles, typically of less than 1 µm in diameter, of active ingredient dispersed in a matrix of hydroxypropyl methylcellulose, as well as systems having small particles of active ingredient dispersed in a matrix of a solid solution of active ingredient in hydroxypropyl methylcellulose. Preferred systems are those wherein the active ingredient is in an essentially non-crystalline phase, as these have an intrinsically faster dissolution rate than those wherein part or all of the active ingredient is in a microcrystalline or crystalline form. The absence of microcrystalline or crystalline active ingredient forms may be ascertained by thermal analysis (DSC) or X-ray diffraction analysis (WARS).

Without wishing to be bound to theory, we believe that polymer "melting" from a crystalline state to nematic "liquid" state generally uses a route which includes a passage via a mesomorphic (liquid crystalline) phase. If the starting hydroxypropyl methylcellulose is incompletely "molten" some mesomorphic domains remain in the polymeric matrix. We believe that the mesomorphic domains have thermodynamic properties, which would place them between melt and crystals and, hence, the endotherm observed at about 240° C. is attributable to the latent heat of transition, i.e., the melting of the mesomorphic domains. The lower the change rate of enthalpy, the lower the proportion of mesomorphic domains in the formulation and the more homogeneous the polymeric matrix. High bioavailability appears to be linked to a highly homogeneous matrix.

Active ingredients used to carry out the present invention are biologically active agents and include those which exert a local physiological effect, as well as those which exert a systemic effect, after oral administration. The invention is particularly useful for water-insoluble or poorly water-soluble (or "lipophilic") compounds. Compounds are considered water-insoluble or poorly water-soluble when their solubility in water at 25° C. is less than 1 g/100 ml. The active ingredient should exhibit a sufficient degree of thermal stability and should not undergo excessive decomposition during preparation of the solid dispersion product, i.e. when heated to a temperature in the range of, for example, about 195° C. to about 300° C.

Examples of suitable active substances include, but are not limited to:
analgesic and anti-inflammatory drugs such as NSAIDs, fentanyl, indomethacin, ibuprofen, ketoprofen, nabumetone, paracetamol, piroxicam, meloxicam, tramadol, and COX-2 inhibitors such as celecoxib and rofecoxib;
anti-arrhythmic drugs such as procainamide, quinidine and verapamil;
antibacterial and antiprotozoal agents such as amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, nortloxacin, ofloxacin, oxacillin, phenoxymethyl-penicillin potassium, pyrimethamine-sulfadoxime and streptomycin;
anti-coagulants such as warfarin;
antidepressants such as amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline and 3-[2-[3,4-dihydrobenzofuro[3,2-c]pyridin-2(1H)-yl]ethyl]-2-methyl-4H-pyrido[1,2-a]pyrimidin-4-one;
anti-diabetic drugs such as glibenclamide and metformin;
anti-epileptic drugs such as carbamazepine, clonazepam, ethosuximide; gabapentin, lamotrigine, levetiracetam, phenobarbitone, phenyloin, primidone, tiagabine, topiramate, valpromide and vigabatrin;
antifungal agents such as amphotericin, clotrimazole, econazole, fluconazole, flucytosine, griseofulvin, ketoconazole, miconazole nitrate, nystatin, terbinafine and voriconazole;
antihistamines such as astemizole, cinnarizine, cyproheptadine, decarboethoxyloratadine, fexofenadine, flunarizine, levocabastine, loratadine, norastemizole, oxatomide, promethazine and terfenadine;
anti-hypertensive drugs such as captopril, enalapril, ketanserin, lisinopril, minoxidil, prazosin, ramipril, reserpine, terazosin and telmisartan;
anti-muscarinic agents such as atropine sulphate and hyoscine;
antineoplastic agents and antimetabolites such as platinum compounds, such as cisplatin and carboplatin; taxanes such as paclitaxel and docetaxel; tecans such as camptothecin, irinotecan and topotecan; vinca alkaloids such as vinblastine, vindecine, vincristine and vinoreibine; nucleoside derivatives and folic acid antagonists such as 5-fluorouracil, capecitabine, gemcitabine, mercaptopurine, thioguanine, cladribine and methotrexate; alkylating agents such as the nitrogen mustards, e.g. cyclophosphamide, chlorambucil, chiormethine, iphosphamide, melphalan, or the nitrosoureas, e.g. carmustine, lomustine, or other alkylating agents, e.g. busulphan, dacarbazine, procarbazine, thiotepa; antibiotics such as daunorubicin, doxorubicin, idarubicin, epirubicin, bleomycin, dactinomycin and mitomycin; HER 2 antibody such as trastuzumab; podophyllotoxin derivatives such as etoposide and teniposide; farnesyl transferase inhibitors; anthrachinon derivatives such as mitoxantron; tyrosine kinase inhibitors such as imatinib;
anti-migraine drugs such as alniditan, naratriptan and sumatriptan;
anti-Parkinsonian drugs such as bromocryptine mesylate, levodopa and selegiline;
antipsychotic, hypnotic and sedating agents such as alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone and zolpidem;
anti-stroke agents such as lubeluzole, lubeluzole oxide, riluzole, aptiganel, eliprodil and remacemide;
antitussives such as dextromethorphan and laevodropropizine;
antivirals such as acyclovir, ganciclovir, loviride, tivirapine, zidovudine, lamivudine, zidovudine/lamivudine, didanosine, zalcitabine, stavudine, abacavir, lopinavir, amprenavir, nevirapine, efavirenz, delavirdine, indinavir, nelfinavir, ritonavir, saquinavir, adefovir and hydroxyurea;
beta-adrenoceptor blocking agents such as atenolol, carvedilol, metoprolol, nebivolol and propanolol;
cardiac inotropic agents such as aminone, digitoxin, digoxin and milrinone;
corticosteroids such as beclomethasone dipropionate, betamethasone, budesonide, dexamethasone, hydrocortisone, methylprednisolone, prednisolone, prednisone and triamcinolone;
disinfectants such as chiorhexidine;
diuretics such as acetazolamide, furosemide, hydrochlorothiazide and isosorbide; enzymes;
essential oils such as anethole, anise oil, caraway, cardamom, *cassia* oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol and thyme;
gastro-intestinal agents such as cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel and sulphasalazine;
haemostatics such as aminocaproic acid;
lipid regulating agents such as atorvastatin, fenofibrate, fenofibric acid, lovastatin, pravastatin, probucol and simvastatin;
local anaesthetics such as benzocaine and lignocaine;
opioid analgesics such as buprenorphine, codeine, dextromoramide, dihydrocodeine, hydrocodone, oxycodone and morphine;

parasympathomimetics and anti-dementia drugs such as AIT-082, eptastigmine, galanthamine, metrifonate, milameline, neostigmine, physostigmine, tacrine, donepezil, rivastigmine, sabcomeline, talsaclidine, xanomeline, memantine and lazabemide;

peptides and proteins such as antibodies, becaplermin, cyclosporine, tacrolimus, erythropoietin, immunoglobulins and insuline;

sex hormones such as oestrogens: conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone and quingestanol acetate;

stimulating agents such as sildenafil;

vasodilators such as amlodipine, buflomedil, amyl nitrite, diltiazem, dipyridanhole, glyceryl trinitrate, isosorbide dinitrate, lidoflazine, molsidomine, nicardipine, nifedipine, oxpentifylline and pentaerythritol tetranitrate;

their N-oxides, their pharmaceutically acceptable acid or base addition salts and their stereochemically isomeric forms.

Pharmaceutically acceptable acid addition salts comprise the acid addition salt forms which can be obtained conveniently by treating the base form of the active ingredient with appropriate organic and anorganic acids.

Active ingredients containing an acidic proton may be converted into their non-toxic metal or amine addition salt forms by treatment with appropriate organic and inorganic bases.

The term addition salt also comprises the hydrates and solvent addition forms which the active ingredients are able to form. Examples of such forms are, for example, hydrates, alcoholates and the like.

The N-oxide forms of the active ingredients comprise those active ingredients in which one or several nitrogen atoms are oxidized to the so-called N-oxide.

The term "stereochemically isomeric forms" defines all possible stereoisomeric forms which the active ingredients may possess. In particular, stereogenic centers may have the R- or S-configuration and active ingredients containing one or more double bonds may have the E- or Z-configuration.

The hydroxpropyl methylcellulose (HPMC) (or combination of HPMCs) used in carrying out the invention contains a sufficient number of hydroxypropyl and methoxy groups to render it water-soluble.

The total content of methoxy and hydroxypropyl groups (or, if a combination of different HPMCs is used, the average total content of methoxy and hydroxypropyl groups) is preferably in the range of 23 to 42% by weight. More preferably, the total content of methoxy and hydroxypropyl groups is in the range of 30 to 42% by weight. Preferably, the methoxy group content is in the range of 19 to 30 wt % (in particular 28 to 30 wt %) and the hydroxypropyl group content is in the range of 4 to 12 wt % (in particular 7 to 12 wt %).

Hydroxypropyl methylcellulose is also known as hypromellose (see Martindale, The Extra Pharmacopoeia, 29$^{th}$ edition (Pharmaceutical Press, 1989) page 1435). For HPMC, three types are commercially available: HPMC 2208, HPMC 2906, and HPMC 2910, depending on the contents of methoxy and hydroxypropyl groups. In the four digit number associated with HPMC as described by Martindale, the first two digits represent the approximate percentage of methoxy groups and the third and fourth digits the approximate percentage composition of hydroxypropyl groups. It is specified that hydroxypropyl methyl cellulose 2208 contains 19 to 24 wt % of methoxy groups and 4 to 12 wt % of hydroxypropyl groups in a total of 23 to 36 wt %; hydroxypropyl methyl cellulose 2906 contains 27 to 30 wt % of methoxy groups and 4 to 7.5 wt % of hydroxypropyl groups in a total of 31 to 37.5 wt %, and hydroxypropyl methyl cellulose 2910 contains 28 to 30 wt % of methoxy groups and 7 to 12 wt % of hydroxypropyl groups in a total of 35 to 42 wt %. Any of these celluloses may be used in the practice of the invention, with HPMC 2910 being especially preferred.

The molecular weight of the HPMC normally affects both the release profile of the milled extrudate as well as its physical properties. A desired release profile can thus be designed by choosing an HPMC of an appropriate molecular weight. For immediate release of the active ingredient from the particles, a low molecular weight polymer is preferred. A high molecular weight HPMC is more likely to yield a sustained release pharmaceutical dosage form. The molecular weight of a water-soluble cellulose ether, such as HPMC, is generally expressed in terms of the apparent viscosity of an aqueous solution containing two percent by weight of said cellulose ether at 20° C. Suitable HPMCs include those having a viscosity from about 1 to about 100 mPa·s, more preferably from about 3 to about 15 mPa·s, and most preferably at about 5 mPa·s. The most preferred type of HPMC having a viscosity of 5 mPas is the commercially available HPMC 2910 5 mPa·s.

Although it is believed that the particle size distribution of the HPMC starting material is of secondary influence to the properties of solid dispersion product, the HPMC starting material preferably has a size distribution (as determined using laser light diffraction; Malvern Mastersizer) with $d_{0.5}$ of not more than 125 μm, more preferably of not more than 100. Preferably, $d_{0.9}$ is not more than 300 μm, more preferably not more than 245 μm.

Preferably, the weight ratio of active ingredient:hydroxypropyl methylcellulose is in the range of 1:1 to 1:17, more preferably 1:1 to 1:5. In the case of (active ingredient):(HPMC 2910 5 mPa·s, this ratio may range from about 1:1 to about 1:2 and is optimally about 1:1.5 (or 2:3). The lower limit is determined by practical considerations. Indeed, given that the therapeutically effective amount of active ingredient is from about 50 mg to about 400 mg per day, preferably 200 mg per day, the lower limit ratio is determined by the maximum amount of mixture that can be processed into one dosage form of a practical size. When the relative amount of water-soluble polymer exceeds the upper acceptable range, the absolute amount of mixture needed to achieve a therapeutic level will be too great to be processed into one capsule or tablet. Tablets, for example, can have a maximum weight of about 1 gram, of which a maximum of 90% (w/w) can be the extrudate. In this case, the lower limit of the amount of active ingredient compared to hydroxypropyl methylcellulose will be about 1:17 (i.e., 50 mg active ingredient and 50 mg polymer).

As the ratio of active ingredient:hydroxypropyl methylcellulose increases (i.e. the amount of active ingredient increases relative to the amount of polymer), then there is the risk that the active ingredient will not dissolve sufficiently in the polymer and thus that the required bioavailability will not be obtained. The degree to which a compound has dissolved in a water-soluble polymer can often be checked visually. If the extrudate is clear, then it is likely that the compound has dissolved completely in the water-soluble polymer. The 1:1 active ingredient:hydroxypropyl methylcellulose upper limit is determined by the fact that it has been observed that, at this ratio, the extrudate resulting from extruding active ingredient with HPMC 2910 5 mPa·s was not "clear", presumably due to the fact that not all of the active ingredient had dissolved in the HPMC. It will be appreciated that the upper limit of 1:1 may be an underestimate for other types of HPMC.

The solid dispersion product of the invention is prepared by a melt-extrusion process.

The melt-extrusion process typically comprises the following steps:
a) blending the active ingredient and hydroxypropyl methylcellulose;
b) heating the blend to obtain a homogeneous melt,
c) forcing the thus obtained melt through one or more nozzles; and
d) allowing the melt to solidify to obtain a solid dispersion product.

Specifically, the method comprises the following steps:
a) blending (i) an effective amount of one active ingredient or a mixture of two or more active ingredients and (ii) an effective amount of a hydroxypropyl methylcellulose or a mixture of two or more hydroxypropyl methylcelluloses;
b) heating the blend, under preset conditions of temperature, shear and throughput rate, to obtain a homogeneous melt;
c) forcing the thus obtained melt through one or more nozzles;
d) allowing the melt to solidify to obtain a solid dispersion product;
e) subjecting a representative sample of the obtained solid dispersion product to differential scanning calorimetry measurement; and, if necessary,
f) adjusting the conditions of temperature, shear and throughput rate used in step b) such that the solid dispersion product satisfies the formula $$0.35 > \Delta H_{tr},$$

preferably $0.20 > \Delta H_{tr}$, more preferably $0.15 > \Delta H_{tr}$, (wherein $\Delta H_{tr}$ represents the endotherm (J/g) accompanying a transition at an endothermic peak temperature in the range of from about 230° C. to about 260° C., preferably in the range of from about 240° C. to about 250° C.).

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt, thus forming a solution, which, upon cooling, may form a solid solution having advantageous dissolution properties.

The melting and/or mixing takes place in an apparatus customarily used for this purpose. Particularly suitable are extruders or kneaders. Suitable extruders include single screw extruders, intermeshing screw extruders or else multi-screw extruders, preferably twin screw extruders, which can be corotating or counterrotating and are optionally equipped with kneading disks. The heart of any twin-screw compounding extruder is its screws. Typically, the screws comprise forward-flighted elements to convey the materials; further, they may comprise reverse-flighted elements to create pressure fields, and kneaders and shear elements to exert a kneading action to the melt. Screws can be made shear intensive or less aggressive based on the number and type of shearing elements integrated into the screw program.

In the method of the invention it is preferred that the melt is subjected to a kneading action in a kneading section of the extruder. The kneading section may be equipped with kneading disks or rotor blades.

The melt ranges from pasty to viscous. Before allowing the melt to solidify, the melt may be moulded into virtually any desired shape. The shaping of the extrudate is conveniently carried out by a calender with two counter-rotating rollers with mutually matching depressions on their surface. A broad range of tablet forms can be attained by using rollers with different forms of depressions. Alternatively, the extrudate is cut into pieces, either before (hot-cut) or after solidification (cold-cut).

In one embodiment the melt is extruded through a slot die to obtain a film. The film thus obtained is optionally stretched, axially or biaxially. The film can be cut into the desired size.

It has been found that the energy input during melt-extrusion production is important for good bioavailability. Based upon the results of the examples that follow, it is postulated that the higher the energy input in the extrusion process, the better the dispersion of the active ingredient in the matrix. A lower endotherm at about 240° C. is indicative of better dispersion.

One of the most important parameters governing energy input during the melt-extrusion process is the temperature at which the melt-extruder is operating and the temperature at which the nozzle or die, through which the melt is forced, is kept. The temperature may vary along the length of the extruder barrel. For the purposes herein, the "operating temperature" is the highest temperature the mixture encounters during its passage through the extruder. It was found that the operating temperature and the nozzle temperature should range between about 195° C. and about 300° C. At temperatures lower than 195° C., the extrudate will not have the required bioavailability. In addition, the process is difficult because of the high viscosity of the mixture. At temperatures of more than 300° C. the hydroxypropyl methylcellulose may decompose to an unacceptable level. The working temperatures will also be determined by the kind of extruder or the kind of configuration within the extruder that is used.

The throughput rate is also of importance. The longer the mixture remains in contact with the heating element, the higher the energy input.

Although most of the energy needed to melt, mix and dissolve the components in the extruder is usually provided by the heating elements, the friction of the material within the extruder may also provide a substantial amount of energy to the mixture and aid in the formation of a homogeneous melt of the components. Thus, variation of the screw speed of the extruder has an impact on the energy input. We have found that typically a screw speed of more than 80 revolutions per minute, preferably of more than 100 revolutions per minute up to 350 revolutions per minute, is required to bring about sufficient mixing and shearing.

It will be appreciated that, based on the explanation above and the examples that follow, the person skilled in the art will be able to select appropriate parameters for the melt extrusion process to produce extrudates that satisfy the above formula pertaining to $\Delta H_{tr}$.

The solid dispersion product may further comprise one or more pharmaceutically acceptable excipients such as, for example, plasticizers, surfactants, flavors, colorants, preservatives and the like. Said excipients should not be heat-sensitive, in other words, they should not show any appreciable degradation or decomposition at the working temperature of the melt-extruder.

The amount of plasticizer is preferably small, in the order of 0% to 15% (w/w), preferably less than 5% (w/w). In particular, no plasticizer is present in the solid dispersion product. Plasticizers as mentioned hereinbelow lower the temperature at which a melt of active ingredient, hydroxypropyl methylcellulose and plasticizer is formed; this lowering of the melting point is sometimes advantageous. Suitable plasticizers are pharmaceutically acceptable and include low molecular weight polyalcohols such as ethylene glycol, propylene glycol, 1,2-butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as sorbitol lactate, ethyl lactate, butyl lactate, ethyl glycolate, allyl glycolate; and amines such as monoethanolamine, diethanolamine, triethanolamine, monoisopropanolamine; triethylenetetramine, 2-amino-2-methyl-1,3-propanediol and the like. Among these, the low molecular weight polyethylene glycols, ethylene glycol, low molecular weight polypropylene glycols and especially propylene glycol are preferred.

The term "pharmaceutically acceptable surfactant" refers to a pharmaceutically acceptable non-ionic surfactant. The surfactant may effect an instantaneous emulsification of the active ingredient released from the dosage form and prevent precipitation of the active ingredient in the aqueous fluids of the gastrointestinal tract. Preferred surfactants are selected from: polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether or polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate or PEG-300 dioleate; alkylene glycol fatty acid mono esters, e.g. propylene glycol monolaurate (Lauroglycol®); sucrose fatty acid esters, e.g. sucrose monostearate, sucrose distearate, sucrose monolaurate or sucrose dilaurate; sorbitan fatty acid mono esters such as sorbitan mono laurate (Span® 20), sorbitan monooleate, sorbitan monopalmitate (Span® 40), or sorbitan stearate, polyoxyethylene castor oil derivates, e.g. polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40) or polyethylenglycol 60 hydrogenated castor oil (Cremophor® RH 60); or block copolymers of ethylene oxide and propylene oxide, also known as polyoxyethylene polyoxypropylene block copolymers or polyoxyethylene polypropyleneglycol such as Poloxamer® 124, Poloxamer® 188, Poloxamer® 237, Poloxamer® 388, or Poloxamer® 407 (BASF Wyandotte Corp.); or mono fatty acid esters of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40), polyoxyethylene (20) sorbitan monolaurate (Tween® 20), or mixtures of one or more thereof.

The solid dispersion product is preferably milled or ground to particles having a particle size of less than 600 µm, preferably less than 400 µm and most preferably less than 125 µm. The particle size proves to be an important factor in determining the speed at which tablets having sufficient hardness can be manufactured on a large scale; the smaller the particles, the higherer the tabletting speed can be without detrimental effects on their quality. The particle size distribution is such that more than 70% of the particles (measured by weight) have a diameter ranging from about 50 µm to about 500 µm, in particular from about 50 µm to about 200 µm and especially from about 50 µm to about 125 µm. Particles with the dimensions mentioned herein can be obtained by sieving them through nominal standard test sieves as described in the CRC Handbook, 64$^{th}$ ed., page F-114. Nominal standard sieves are characterized by the mesh/hole width (µm), DIN 4188 (mm), ASTM E 11-70 (No), Tyler® (mesh) or BS 410 (mesh) values. Throughout this description, particle sizes are designated by reference to the mesh/hole width in µm and to the corresponding Sieve No, in the ASTM E11-70 standard.

Once the extrudate is obtained, it is milled and sieved and used as a "normal" ingredient to make pharmaceutical dosage forms.

The particles of the solid dispersion product can be formulated into pharmaceutical dosage forms comprising a therapeutically effective amount of particles. Although mainly pharmaceutical dosage forms for oral administration such as tablets and capsules are envisaged, the particles of the present invention can also be used to prepare pharmaceutical dosage forms e.g. for rectal administration. Preferred dosage forms are those adapted for oral administration shaped as a tablet. They can be produced by conventional tabletting techniques with conventional ingredients or excipients and with conventional tabletting machines. In addition, they can be produced at substantially lower cost than the coated cores. Preferably, the (milled) solid dispersion product accounts for not less than 40 wt. % of the weight of the final dosage form, in particular from 45 to 90 wt. %.

In order to facilitate the swallowing of such a dosage form by a mammal, it is advantageous to give the dosage form, in particular tablets, an appropriate shape. Tablets that can be swallowed comfortably are therefore preferably elongated rather than round in shape. Especially preferred are biconvex oblate tablets. As discussed below in more detail, a film coat on the tablet further contributes to the ease with which it can be swallowed.

Tablets that give an immediate release of the active ingredient upon oral ingestion and that have good bioavailability are designed in such a manner that the tablets disintegrate rapidly in the stomach (immediate release) while keeping the particles liberated in the process away from one another so that they do not coalesce, create local high concentrations of the active ingredient and increase the chances that the drug precipitates (bioavailability). The desired effect can be obtained by distributing said particles homogeneously throughout a mixture of a disintegrant and diluent.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose (crosslinked sodium carboxymethylcellulose). The amount of disintegrant in immediate release tablets according to the present invention may conveniently range from about 3 to about 15% (w/w) and is preferably about 7 to 9%, in particular about 8.5% (w/w). This amount tends to be greater in tablets in order to ensure that the particles are spread throughout a large volume of the stomach contents upon ingestion. Because disintegrants by nature yield sustained release formulations when employed in bulk, it is advantageous to dilute them with an inert substance called a diluent or filler.

A variety of materials may be used as diluents or fillers. Examples are spray-dried or anhydrous lactose, sucrose, dextrose, mannitol, sorbitol, starch, cellulose (e.g. microcrystalline cellulose Avicel®), dihydrated or anhydrous dibasic calcium phosphate, and others known in the art, and mixtures thereof. A commercial spray-dried mixture of lactose monohydrate (75%) with microcrystalline cellulose (25%), which is commercially available as Microcelac®, is preferred. The amount of diluent or filler in the tablets may conveniently range from about 20% to about 40% (w/w) and preferably ranges from about 25% to about 32% (w/w).

The tablet may include a variety of one or more other conventional excipients such as binders, buffering agents, lubricants, glidants, thickening agents, sweetening agents, flavors, and colors. Some excipients can serve multiple purposes.

Lubricants and glidants can be employed in the manufacture of certain dosage forms, and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, talc, mixtures thereof, and others known in the art. Interesting lubricants and glidants are magnesium stearate, and mixtures of magnesium stearate with colloidal silica. A preferred lubricant is hydrogenated vegetable oil type I, most preferably hydrogenated, deodorized Cottonseed oil (commercially available from Karlshamns as Akofine NF® (formerly called Sterotex®). Lubricants and glidants generally comprise 0.2 to 7.0% of the total tablet weight.

Other excipients such as coloring agents and pigments may also be added to the tablets of the present invention. Coloring agents and pigments include titanium dioxide and dyes suitable for food. A coloring agent is an optional ingredient in the tablet of the present invention, but, when used, the coloring agent can be present in an amount of up to 3.5% based on the total tablet weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount of from about 0% to about 3% (w/w).

As known in the art, tablet blends may be dry-granulated or wet-granulated before tabletting. The tabletting process itself is otherwise standard and readily practiced by moulding a tablet from a desired blend or mixture of ingredients into the appropriate shape using a conventional tablet press.

Tablets of the present invention may further be film-coated to improve taste or provide ease of swallowing and an elegant appearance. Many suitable polymeric film-coating materials are known in the art. A preferred film-coating material is hydroxypropyl methylcellulose HPMC, especially HPMC 2910 5 mPa·s. Other suitable film-forming polymers also may be used herein, including hydroxypropylcellulose and acrylate-methacrylate copolymers. Besides a film-forming polymer, the film coat may further comprise a plasticizer (e.g. propylene glycol) and, optionally, a pigment (e.g. titanium dioxide). The film-coating suspension also may contain talc as an anti-adhesive. In immediate release tablets according to the invention, the film coat is small and in terms of weight accounts for less than about 3% (w/w) of the total tablet weight.

Preferred dosage forms are those wherein the weight of the particles is at least 40% of the total weight of the total dosage form, the weight of the diluent ranges from 20 to 40%, and the weight of the disintegrant ranges from 3 to 10%, the remainder being accounted for by one or more of the excipients described above.

We claim:
1. A solid dispersion product comprising
   (i) an effective amount of one active ingredient or a mixture of two or more active ingredients and
   (ii) an effective amount of a hydroxypropyl methylcellulose or a mixture of two or more hydroxypropyl methylcelluloses, wherein said solid dispersion product satisfies the formula

$$0.35 > \Delta H_{tr}$$

wherein $\Delta H_{tr}$ represents the endotherm (J/g) accompanying a transition at an endothermic peak temperature in the range of from about 230° C. to about 260° C., and wherein said transition is the melting of mesomorphic domains of the hydroxypropyl methylcellulose(s).

2. The solid dispersion product of claim 1, which satisfies the formula $$0.20 > \Delta H_{tr}$$

wherein $\Delta H_{tr}$ represents the endotherm (J/g) accompanying a transition at an endothermic peak temperature in the range of from about 230° C. to about 260° C.

3. The solid dispersion product of claim 1, which satisfies the formula $$0.15 > \Delta H_{tr}$$

wherein $\Delta H_{tr}$ represents the endotherm (J/g) accompanying a transition at an endothermic peak temperature in the range of from about 230° C. to about 260° C.

4. The solid dispersion product of claim 1, wherein the endothermic peak temperature is in the range of from about 240° C. to about 250° C.

5. The solid dispersion product of claim 1, having a weight-average particle size of less than 600 μm.

6. The solid dispersion product of claim 1, wherein the total content of methoxy and hydroxypropyl groups in the hydroxypropyl methylcellulose is in the range of 23 to 42% by weight.

7. The solid dispersion product of claim 6, wherein the methoxy group content is in the range of 19 to 30 wt % and the hydroxypropyl group content is in the range of 4 to 12% by weight.

8. The solid dispersion product of claim 7, wherein the hydroxypropyl methylcellulose has an apparent viscosity of from about 3 to about 15 mPa·s, as determined as a 2 wt. % aqueous solution at 20° C.

9. The solid dispersion product of claim 1, wherein the weight ratio of active ingredient to hydroxypropyl methylcellulose is in the range of 1:1 to 1:17.

10. A pharmaceutical dosage form comprising particles of the solid dispersion product of claim 1 and at least one additive selected from the group consisting of a diluent and a disintegrant.

11. A method for preparing a solid dispersion product, which comprises:
   a) blending (i) an effective amount of one active ingredient or a mixture of two or more active ingredients and (ii) an effective amount of a hydroxypropyl methylcellulose or a mixture of two or more hydroxypropyl methylcelluloses;

b) heating the blend, under preset conditions of temperature, shear and throughput rate, to obtain a homogeneous melt;

c) forcing the thus obtained melt through one or more nozzles;

d) allowing the melt to solidify to obtain a solid dispersion product;

e) subjecting a representative sample of the obtained solid dispersion product to differential scanning calorimetry measurement; and, if necessary, e) adjusting the conditions of temperature, shear and throughput rate used in step b) such that the solid dispersion product satisfies the formula $$0.35 > \Delta H_{tr}$$

wherein $\Delta H_{tr}$ represents the endotherm (J/g) accompanying a transition at an endothermic peak temperature in the range of from about 230° C. to about 260° C., and wherein said transition is the melting of mesomorphic domains of the hydroxypropyl methylcellulose(s).

12. The method of claim 11, wherein step b) is carried out in an extruder and the blend is subjected to a kneading action in a kneading section of the extruder.

13. The method of claim 11, wherein step b) is carried out in an extruder, the extruder operating temperature and the nozzle temperature being in the range of from about 195° C. to about 300° C.

14. The method of claim 11, wherein the total content of methoxy and hydroxypropyl groups in the hydroxypropyl methylcellulose is in the range of 23 to 42% by weight.

15. The method of claim 14, wherein the methoxy group content is in the range of 19 to 30 wt % and the hydroxypropyl group content is in the range of 4 to 12% by weight.

16. The method of claim 15, wherein the hydroxypropyl methylcellulose has an apparent viscosity of from about 3 to about 15 mPa·s, as determined as an 2 wt. % aqueous solution at 20° C.

17. The method of claim 11, wherein the weight ratio of active ingredient:hydroxypropyl methylcellulose is in the range of 1:1 to 1:17.

18. The method of claim 11, additionally comprising grinding the solid dispersion product.

19. The method of claim 18, additionally comprising sieving the ground solid dispersion product.

20. The method of claim 18, additionally comprising compressing the ground solid dispersion product into a tablet.

21. A process for the manufacture of a dosage form having improved bioavailability of one or more active ingredients by oral administration to a patient in need thereof, said process comprising preparing a solid dispersion product by blending (i) an effective amount of one active ingredient or a mixture of two or more active ingredients and (ii) an effective amount of a hydroxypropyl methylcellulose or a mixture of two or more hydroxypropyl methylcelluloses, wherein said solid dispersion product satisfies the formula $$0.35 > \Delta H_{tr}$$

wherein $\Delta H_{tr}$ represents the endotherm (J/g) accompanying a transition at an endothermic peak temperature in the range of from about 230° C. to about 260° C., and wherein said transition is the melting of mesomorphic domains of the hydroxypropyl methylcellulose(s).

22. The process of claim 21, wherein said solid dispersion product satisfies the formula $$0.20 > \Delta H_{tr}$$

wherein $\Delta H_{tr}$ represents the endotherm (J/g) accompanying a transition at an endothermic peak temperature in the range of from about 230° C. to about 260° C.

23. The process of claim 21, wherein said solid dispersion product satisfies the formula $$0.15 > \Delta H_{tr}$$

wherein $\Delta H_{tr}$ represents the endotherm (J/g) accompanying a transition at an endothermic peak temperature in the range of from about 230° C. to about 260° C.

24. The process of claim 21, wherein the endothermic peak temperature is in the range of from about 240° C. to about 250° C.

25. The process of claim 21, wherein the solid dispersion product is comprised of particles having a weight-average particle size of less than 600 μm.

26. The process of claim 21, wherein the total content of methoxy and hydroxypropyl groups in the hydroxypropyl methylcellulose is in the range of 23 to 42% by weight.

27. The process of claim 26, wherein the methoxy group content is in the range of 19 to 30 wt % and the hydroxypropyl group content is in the range of 4 to 12% by weight.

28. The process of claim 27, wherein the hydroxypropyl methylcellulose has apparent viscosity of from about 3 to about 15 mPa·s, as determined as an 2 wt. % aqueous solution at 20° C.

29. The process of claim 21, wherein the weight ratio of active ingredient: hydroxypropyl methylcellulose is in the range of 1:1 to 1:17.

30. The method of claim 11, wherein the solid dispersion product satisfies the formula $$0.20 > \Delta H_{tr}$$

31. The method of claim 11, wherein the solid dispersion product satisfies the formula $$0.15 > \Delta H_{tr}$$

* * * * *